United States Patent [19]

Jensen

[11] 4,110,848

[45] Sep. 5, 1978

[54] INTRAOCULAR LENS FOR IMPLANTATION INTO THE POSTERIOR CHAMBER OF A HUMAN EYE

[75] Inventor: Ronald P. Jensen, 4156 Dorset Pl., Pasadena, Calif. 91103

[73] Assignee: Ronald P. Jensen, Glendale, Calif.

[21] Appl. No.: 794,467

[22] Filed: May 6, 1977

[51] Int. Cl.² ............................ A61F 1/16; A61F 1/24
[52] U.S. Cl. ........................................................... 3/13
[58] Field of Search ........................................ 3/13, 1

[56] References Cited

U.S. PATENT DOCUMENTS

| | | | |
|---|---|---|---|
| 3,906,551 | 9/1975 | Otter | 3/13 |
| 3,925,825 | 12/1975 | Richards et al. | 3/13 |
| 3,994,027 | 11/1976 | Jensen et al. | 3/13 |

FOREIGN PATENT DOCUMENTS

| | | | |
|---|---|---|---|
| 810,232 | 3/1959 | United Kingdom | 3/13 |

*Primary Examiner*—Ronald L. Frinks

*Attorney, Agent, or Firm*—W. Edward Johansen

[57] ABSTRACT

The present invention is an intraocular lens for implantation into the posterior chamber of a human eye. The intraocular lens includes a plano-convex lens, which is formed from an optical material that is suitable for an implantable lens. The plano-convex lens is adapted to be inserted into the posterior chamber of the human eye within the capsular membrane thereof. The intraocular lens also includes a first supporting loop and a second supporting loop, which are formed from a material that is suitable for implantation into the eye, mechanically coupled to the peripheral edge of plano-convex lens and disposed at an angle in the range of 0° to 25° to the plane surface of the plano-convex lens so that their end portions are below the plane surface of the plano-convex lens. The second supporting loop has a notch which is disposed between the peripheral edge of the plano-convex lens and its end portions so that a temporary securement to the iris of the human eye may be accomplished.

4 Claims, 4 Drawing Figures

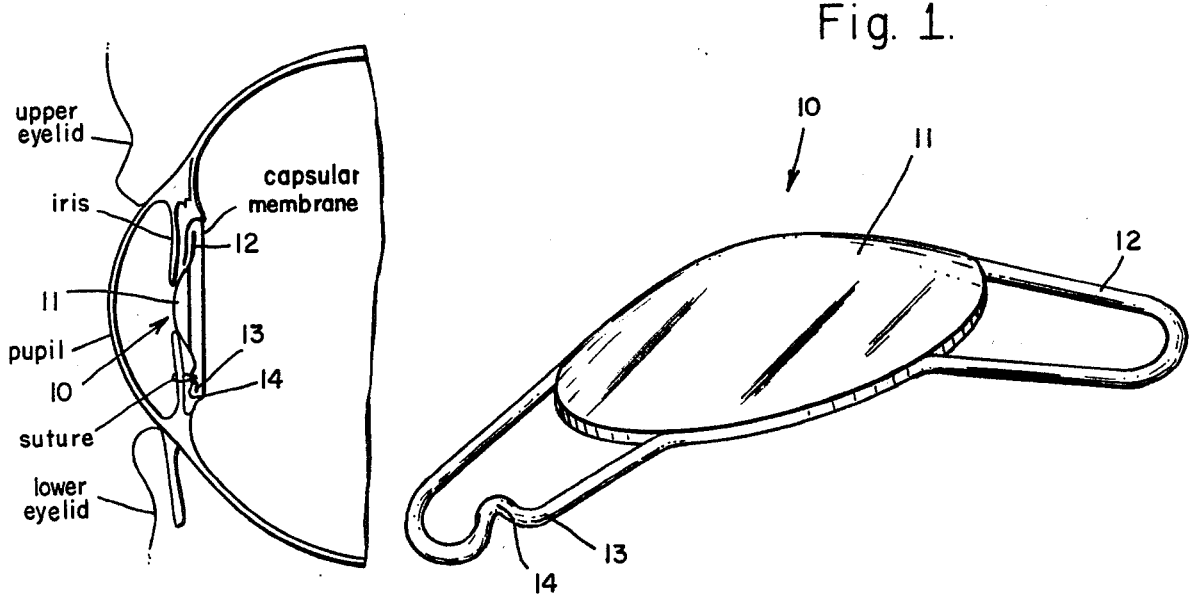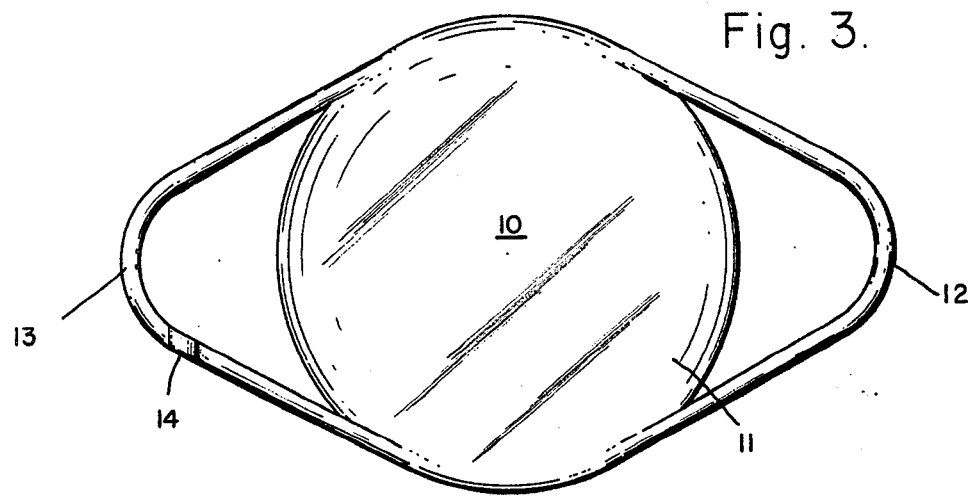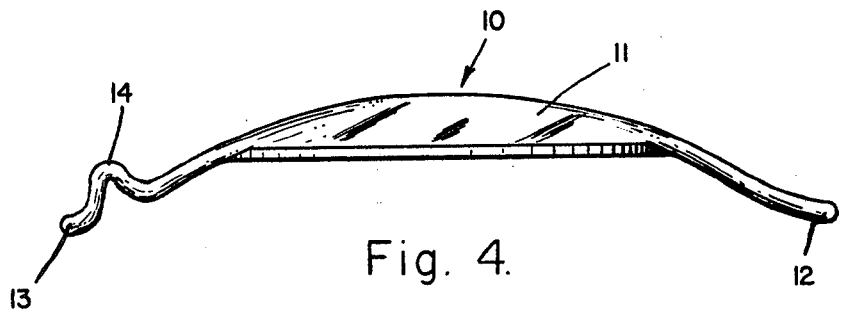

INTRAOCULAR LENS FOR IMPLANTATION INTO THE POSTERIOR CHAMBER OF A HUMAN EYE

BACKGROUND OF THE INVENTION

1. Field of the Invention

The present invention relates to an improved prepupillary lens which may be surgically implanted into the posterior chamber of a human eye and more particularly to a method for securing the lens within the chamber.

2. Description of the Prior Art

In the prior art prepupillary lenses have been used in an operation for surgically implanting a lens on the iris of a human eye. Cornelius D. Binkhorst, M. D., who has performed this operation since 1958, has used a two-loop lens and a four-loop lens. He has described both of these lenses in an article entitled, "The Iridocapsular (Two-loop) Lens and the Iris-clip (Four-loop) Lens in Pseudophakia", which he wrote for the 1973 September-October edition of Transactions of the American Academy of Opthalmolgy and Otolaryngology. These lenses are made from a plastic material, ploymethyl methacrylate, which is commonly used to make contact lenses. The lenses are in the shape of a plano convex lens and have a diameter of 5.0 millimeters and a central thickness of from 0.5 millimeters to 0.6 millimeters depending on the required lens strength.

U.S. Pat. No. 3,994,027, entitled Prepupillary Lens for Implanting in a Human Eye, issued to Ronald P. Jensen and James Fetz on Nov. 30, 1976 teaches a two-loop lens which has its loops buried in the posterior chamber of the human eye, but which rests within the anterior chamber of the human eye. The difficulty with this position of the two-loop lens is that this is not the normal position of the original lens. The placement of the lens in the anterior chamber of the human eye is unnatural and creates a problem in the restoration of accurate binocular vision. Further the lens in the anterior chamber is not adjacent to the hyloid membrane for supporting the vitreous humor thereby making instances of forward displacement of the vitreous humor and retinal detachment more likely to occur.

U.S. Pat. No. 3,866,249, entitled Posterior Chamber Artificial Intraocular Lens, issued to Leonard Flom on Feb. 18, 1975, teaches an artificial intraocular lens for implantation in the posterior chamber of an eye which includes an optical zone portion fabricated of transparent material and shaped similar to a natural lens and a plurality of prongs attached to the optical zone portion near its periphery. The prongs protrude forwardly therefrom for insertion through the iris of the eye to hold and position the lens therein. The difficulty with this lens is that it is affixed to the iris of the eye and therefore it is not rigidly anchored thereby allowing the lens to move with eye movement. Subsequently, the iris may erode and the fixation of the lens may be lost. It would far better to anchor the intraocular lens within the posterior chamber to the capsular membrane which is a very firm, non-viable tissue and which provides firm, secure and permanent fixation of the lens.

U.S. Pat. No. 3,711,870, entitled Artificial Lens Implant, issued to Rollin E. Deitrick on Jan. 23, 1973, teaches a lens for implantation in the eye which has a resilient flange that is sutured to the ciliary muscle of the eye to position and to retain the lens in the same position as the original lens. This lens irritates the ciliary body so that inflammation is likely to occur. The fixation of the lens to the ciliary body is not only a difficult surgical procedure, but also does not provide a firm, secure of permanent fixation of the lens.

U.S. Pat. No. 3,913,148, entitled Intraocular Lens Apparatus, issued to Ernst W. Potthast on Oct. 21, 1975, U.S. Pat. No. 3,991,426, entitled Posterior Chamber Artificial Intraocular Lens with Retaining Means and Instruments for Use Therewith, issued to Leonard Flom and Kenneth J. Rodgerson on Nov. 16, 1976, and U.S. Pat. No. 4,014,049, entitled Artificial Intraocular Lens and Supporting System Therefor, all teach intraocular lenses that are positioned in the posterior chamber of the eye and that are fixated to the iris of the eye.

SUMMARY OF THE INVENTION

In view of the foregoing factors and conditions of the prior art it is a primary object of the present invention to provide an intraocular that is positioned in the posterior chamber and is anchored securely in the capsular membrane formed by the anterior and posterior capsules adhering together.

It is another object of the present invention to provide an intraocular lens that requires only one, temporary securement to the iris of the eye until capsular fixation occurs.

It is still another object of the present invention to provide an intraocular lens for implantation into the capsular membrane that does not have a supporting member which protrudes above the iris so that in the future glaucoma surgery may be perfomed and additionally so that the iris is free to move in a normal manner.

It is yet another object of the present invention to provide an intraocular lens for implantation in the posterior chamber which will eliminate edge reflection which occurs in the lenses implanted in the anterior chamber and which will minimize internal reflection by eliminating the posts required by the other posterior lenses.

It is yet still another object of the present invention to provide an intraocular lens for implantation in the posterior chamber that is not only a strong and secure fixation, but also a lifetime fixation.

In accordance with an embodiment of the present invention an intraocular lens for implantation into the posterior chamber of a human eye is described. The intraocular lens includes a plano-convex lens, which is formed from an optical material that is suitable for an implantable lens. The plano-convex is adapted to be inserted into the posterior chamber of the human eye within the capsular membrane thereof. The intraocular lens also includes a first supporting loop and a second supporting loop, which are fomed from a material that is suitable for implantation into the eye, mechanically coupled to the peripheral edge of the plano-convex lens and disposed at an angle in the range of 0° to 25° to the plane surface of the plano-convex lens so that their end portions are below the plane surface of plano-convex lens. The second supporting loop has a notch which is disposed between the peripheral edge of the plano-convex lens and its end portion so that a temporary securement to the iris of the human eye may be accomplished. In the preferred embodiment of the present invention the plano-convex lens and the first and second supporting loops are molded into one integral member.

The features of the present invention which are believed to be novel are set forth with particularity in the appended claims.

Other claims and many of the attendant advantages will be more readily appreciated as the same becomes better understood by reference to the following detailed description and considered in connection with the accompanying drawing in which like reference symbols designate like parts throughout the figures.

DESCRIPTION OF THE DRAWING

FIG. 1 is a perspective drawing of an intraocular lens which has been constructed in accordance with the principles of the present invention.

FIG. 2 is a schematic drawing of a human eye in which an intraocular lens of FIG. 1 has been implanted within the posterior chamber thereof.

FIG. 3 is a plan view of the intraocular lens of FIG. 1.

FIG. 4 is a side elevational view of intraocular lens of FIG. 1.

DESCRIPTION OF THE PREFERRED EMBODIMENT

In order to best understand the present invention a description of the preferred embodiment thereof is provided accompanied by a drawing. In FIG. 1 a perspective view of an intraocular lens 10 for implantation in the posterior chamber of a human eye is shown. The intraocular lens 10 has a plano-convex lens, which is formed from an optical material that is suitable for an implantable lens, which is adapted to be inserted into the posterior chamber of the human eye within the capsular membrane thereof. The optical material most commonly used is polymethyl methacrylate. The intraocular lens 10 also has a first supporting loop 12, which is formed from a material that is suitable for implantation into the eye, mechanically cupled to the peripheral edge of the plano-convex lens 11 and disposed at an angle in the range of 0° to 25° to the plane surface of the plano-convex lens 11 so that its end portion is below the surface thereof. The intraocular lens 10 further has a second supporting loop 13, which is also formed from a material that is suitable for implantation into the eye, mechanically coupled to the peripheral edge of the plano-convex lens 11 and disposed at an angle in the range of 0° to 25° to the plane surface of the plan-convex lens 11 so that its end portion is below the surface thereof. The second supporting loop 13 has a notch 14 which is disposed between its end portion and the peripheral edge of the plano-convex lens 11.

In the preferred embodiment the first and second supporting loops 12 and 13 are formed from the same material that the plano-convex lens 11 is formed from and combine with the plano-convex lens 11 to form an integral, molded intraocular lens 10.

Other embodiments of the intraocular lens 10 may be made by substituting metal wire or Supramid wire and by attaching the wire to the plano-convex lens 11 by the methods taught in U.S. Pat. No. 3,994,027, which has been mentioned in the Description of the Prior Art.

Referring now to FIG. 2 a schematic drawing of the intraocular lens 10 shows it after it has been implanted into the capsular membrane of a human eye. One should note that a portion of the capsular membrane has been removed so that the intraocular lens 10 may be inserted behind the iris. The first supporting loop 12 is placed in a pocket of the remaining portion of the capular membrane. The anterior side this pocket and the posterior side of this pocket eventually scar together thereby securing the intraocualar within the posterior chamber.

The inventor is an opthalmologist and has implanted both posterior chamber intraocular lenses and anterior chamber lenses. In conjunction with this intraocular lens patent application he has commissioned a tool for implanting this intraocular lens. This tool is the subject of a patent application entitled Intraocular Lens Implantation Tool and filed by Clarence L. Hagar on Aug. 8, 1977 with the patent application being given Ser. No. 822,511.

The inventor has inserted this lens 10 through the iris of a human eye into the capsular membrane so that the first supporting loop 12 slides into the pocket of the capsular membrane. He has then pulled the iris around the second supporting loop 13 so that the entire intraocular lens 10 could be placed into the posterior chamber of the human eye. He has then sutured the notch 14 of the second supporting loop 13 to the iris in order to provide a temporary securement to the iris for the intraocular lens 10. Once the posterior side and the anterior side of the pocket of the capsular membrane have scarred together there is no further need for suture coupling the notch 14 to the iris because the intraocular lens 10 is firmly, permanently and securely fixated to the capsular membrane. Furthermore the iris is free to function normally. The notch 14 may be sutured to the capsular membrane.

The use of the integral, molded member eliminates edge reflections which occur in lenses implanted in the anterior chamber and internal reflections which are caused by the posts for the supporting loops in other lenses implanted in the posterior chamber. Finally the use of this posterior intraocular lens 10 allow the patient to have glaucoma surgery in the future.

Referring now to FIG. 3 and FIG. 4 the intraocular lens 10 is shown in a plan view and a side elevational view. The purpose of hollow portion inside the first and second supporting loops 12 and 13 is not only to allow the implant surgeon to insert his implant tool beneath the lens 10 in order to support the lens 10 during its insertion into the capsular membrane, but also to facilitate the scarring of the posterior side and the anterior side of the pocket of the capsular membrane. The position of the notch 14 in the second supporting loop 13 should not be above the plano-convex lens 11, but it should be adjacent to or above the plane surface of the plano-convex lens 11.

From the foregoing it can be seen that an integral, molded intraocular lens for implantation into the posterior chamber of the human eye has been provided. It should be noted that the sketches are not drawn to scale and that thicknesses and distances of and between figures are not to be considered significant.

Accordingly it is intended that the foregoing disclosure and showing made in the drawing shall be considered only an illustration of the principles of the present invention. The invention will be set out with particularity in the appended claims.

What is claimed is:

1. An intraocular lens for implantation in the posterior chamber of a human eye, said intraocular lens comprising:

a. a plano-convex lens, which is formed from an optical material that is suitable for an implantable lens, which is adapted to be inserted into the posterior chamber of the human eye within the capsular membrane thereof;

b. a first supporting loop, which is formed from a material that is suitable for implantation into the eye, mechanically coupled to the peripheral edge of said plano-convex lens and disposed at an angle in the range of 0° to 25° to the plane surface of said plano-convex lens so that its end portion is below the plane surface of said plano-convex lens, said first supporting loop adapted to secure said plano-convex lens rigidly and permanently in the posterior chamber of the human eye; and c. a second supporting loop, which is formed from a material that is suitable for implantation into the eye, mechanically coupled to the peripheral edge of said plano-convex lens and oppositely disposed to said first supporting loop, said second supporting loop being also disposed at an angle in the range of 0° to 25° to the plane surface of said plano-convex lens so that its end portion is below the plane surface of said plano-convex lens and having a notch which is disposed between its end portion and the peripheral edge of said plano-convex lens so that a temporary securement to the iris of the human eye may be accomplished, said second supporting loop also adapted to secure said plano-convex lens rigidly and permanently in the posterior chamber of the human eye.

2. An intraocular lens for implantation in the posterior chamber of a human eye according to claim 1, wherein said intraocular lens is an integral, molded member.

3. An intraocular lens for implantation in the posterior chamber of a human eye according to claim 1 wherein said first and second supporting loops are formed from Supramid wire.

4. An intraocular lens for implantation in the posterior chamber of a human eye according to claim 1 wherein said first and second supporting loops are formed from metal wire.

* * * * *